(12) United States Patent
Shimon (10) Patent No.: US 7,232,453 B2
(45) Date of Patent: Jun. 19, 2007

(54) ENDOVASCULAR DEVICE FOR ENTRAPMENT OF PARTICULATE MATTER AND METHOD FOR USE

(75) Inventor: Dov V. Shimon, Mevasseret -Zion (IL)

(73) Assignee: Sagax, Inc., Herzlyia Pituach (IL)

( * ) Notice: Subject to any disclaimer, the term of this patent is extended or adjusted under 35 U.S.C. 154(b) by 592 days.

(21) Appl. No.: 10/310,149

(22) Filed: Dec. 5, 2002

(65) Prior Publication Data

US 2003/0171803 A1 Sep. 11, 2003

Related U.S. Application Data

(60) Provisional application No. 60/335,838, filed on Dec. 5, 2001.

(51) Int. Cl.
*A61M 29/00* (2006.01)
(52) U.S. Cl. ............ 606/200; 623/1.12; 623/1.24
(58) Field of Classification Search ......... 606/108, 606/191, 195, 198, 200; 623/1.11, 1.12, 623/1.15, 1.32
See application file for complete search history.

(56) References Cited

U.S. PATENT DOCUMENTS

| 4,873,978 | A |   | 10/1989 | Ginsburg |
|---|---|---|---|---|
| 5,234,458 | A |   | 8/1993 | Metais |
| 5,617,878 | A | * | 4/1997 | Taheri ............... 128/898 |
| 5,769,816 | A |   | 6/1998 | Barbut et al. |
| 5,800,457 | A |   | 9/1998 | Gelbfish |
| 5,814,064 | A |   | 9/1998 | Daniel et al. |
| 5,827,324 | A |   | 10/1998 | Cassell et al. |
| 5,925,063 | A | * | 7/1999 | Khosravi ............ 606/200 |
| 5,928,261 | A | * | 7/1999 | Ruiz ................ 606/200 |
| 6,176,873 | B1 |   | 1/2001 | Ouchi |
| 6,200,336 | B1 |   | 3/2001 | Pavcnik et al. |
| 6,258,120 | B1 |   | 7/2001 | McKenzie et al. |
| 6,267,777 | B1 | * | 7/2001 | Bosma et al. ............ 606/200 |
| 6,409,750 | B1 | * | 6/2002 | Hyodoh et al. ........... 623/1.1 |
| 6,733,525 | B2 | * | 5/2004 | Yang et al. ............. 623/18 |
| 6,939,361 | B1 | * | 9/2005 | Kleshinski .............. 606/200 |

OTHER PUBLICATIONS

PCT International Search Report, International Application No. PCT/IL02/00984.

* cited by examiner

*Primary Examiner*—Michael J. Hayes
*Assistant Examiner*—Victor Nguyen
(74) *Attorney, Agent, or Firm*—Pearl Cohen Zedek Latzer, LLP (57) ABSTRACT

A device and method for protecting a blood vessel, and hence bodily tissues, against damage caused by particulate such as an embolus. The device may be a stent, for insertion in a large artery such as the ascending aorta, and may be combined with a filter. In one embodiment, the device includes an outer wire frame rather than a stent. The stent may be made of at least one layer of mesh, which is typically attached or mounted to the arterial wall. Typically only part of the stent is attached (for example at a reinforcing ring structure). Typically the size of the apertures of the mesh at the top portion of the stent is smaller than the bottom portion of the stent. The device and method are particularly useful in preventing blockages of flow to the brain, but have other uses as well. An electric charge may be placed on the device, for example, to prevent blood components from collecting.

19 Claims, 7 Drawing Sheets

ENDOVASCULAR DEVICE FOR ENTRAPMENT OF PARTICULATE MATTER AND METHOD FOR USE

PRIOR PROVISIONAL APPLICATION

The present application claims benefit from prior provisional application No. 60/335,838 entitled "Endovascular Device for Entrapment of Emboli" and filed on 5 Dec. 2001.

FIELD OF THE INVENTION

The present invention relates to an endovascular device and method for use, and in particular, to a device for trapping particulate such as emboli.

BACKGROUND OF THE INVENTION

Emboli form, for example, as a result of the presence of particulate matter in the bloodstream. Vascular emboli are a major single causative agent for multiple human pathologies. It is a leading cause of disability and death. Clots or thrombi that become dislodged from the point of origin are termed emboli.

Such particulate matter may originate from a blood clot occurring in the heart. It may be a foreign body, but may also be derived from body tissues. For example, atherosclerosis, or hardening of the blood vessels from fatty and calcified deposits, may cause particulate emboli to form. Moreover, clots can form on the luminal surface of the atheroma, as platelets, fibrin, red blood cells and activated clotting factors may adhere to the surface of blood vessels to form a clot.

Blood clots or thrombi may also form in the veins of subjects who are immobilized, particularly in the legs of bedridden or other immobilized patients. These clots may then travel in the bloodstream, potentially to the arteries of the lungs, leading to a common, often-deadly disease called 'pulmonary embolus'. Thrombus formation, and subsequent movement to form an embolus, may occur in the heart or other parts of the arterial system, causing acute reduction of blood supply and hence ischemia. The ischemic damage often leads to tissue necrosis of organs such as the kidneys, retina, bowel, heart, limbs, brain or other organs, or even death.

Since emboli are typically particulate in nature, various types of filters have been proposed in an attempt to remove or divert such particles from the bloodstream before they can cause damage to bodily tissues.

For example, U.S. Pat. No. 6,258,120 discloses a filter device intended to be inserted into the artery of a patient. However, the device has an inherent drawback, which is that the actual trapping of an embolus, for successful operation of the device, may result in blockage of blood flow through the device and hence through the artery. Other disclosed embodiments of the device, which may not be blocked by clots, are not able to filter clots, and may in fact funnel such particulate matter to the blood vessels leading to the brain. None of the disclosed embodiments of the device is anchored to the artery, but instead rely upon conformation to the arterial shape and size to maintain the position of the device, which is not secure. In view of the natural force of blood pressure and elastic recoil of the arterial wall, proper placement and control of position of the device are of paramount importance. If the device moves even slightly, it may even block the artery which it is intended to protect. Such movement may be caused by blood flow for example, as the blood pulse moves through the artery.

U.S. Pat. Nos. 4,873,978, 5,814,064, 5,800,457, 5,769,816, and 5,827,324 describe devices that are intended only for temporary insertion into a blood vessel. Therefore, these devices avoid the difficult issue of simultaneously successfully filtering emboli while also maintaining blood flow through the blood vessel. As such, they do not address the problem of prolonged filtration of the blood.

U.S. Pat. No. 5,234,458 appears to disclose a filter device that is intended to be left in the vessel for a period of time. However, the disclosed filter device lacks a tapered shape, thus introduction and positioning may be unsafe and complex. Such a device does not feature a sufficiently strong anchoring system and the filter does not include a mesh.

The lack of a suitable anchoring system is a general problem with devices disclosed in the background art, as the pulsating blood flow, aortic elasticity and movement may all cause a device inserted into a major blood vessel to become dislodged. Furthermore, those devices which feature rigid structures may create turbulent blood flow at certain locations such as the aortic arch, leading to decreased cerebral blood flow and possible activation of the clotting mechanism.

Therefore, there is a need for a more effective and safer device and method for protecting against particulate such as emboli.

SUMMARY OF THE INVENTION

Embodiments of the present invention provide for a device and method for protecting a blood vessel, and hence bodily tissues, against damage caused by particulate such as an embolus. The device is typically a stent, for insertion in a large artery such as the ascending aorta (as shown below), aortic arch or any artery in jeopardy, and is structured as a filter and/or with filtering material. Other configurations can be used. The filtering structure is typically made of at least one layer of mesh, which may be attached to the arterial wall. Typically only part of the device is attached (for example at a reinforcing structure or a ring structure).

In one embodiment, the outer structure is a wire frame.

A device according to an embodiment of the present invention may feature plurality of layers. The outer layer is typically made of a dilatable and/or otherwise self-expanding tubular structure. This tubular structure is typically anchored to the vascular wall after dilation to the size and shape of the vessel, or to the diameter of the blood vessel. Anchoring components, such as fine pins, may be employed for anchoring the device to the tissues of the vascular wall. The material of which the device is constructed may optionally be metallic. Other materials may be used.

According to one embodiment, the device includes a first typically outer cage-like structure (such as a stent) for holding an inner net. The net is able to filter the particulate matter. More typically, at least the net is manufactured from a flexible thread such as surgical monofilament sutures suitable for insertion into the body and/or for medical use. Other materials may be used. For example, metallic material, such as titanium, gold, and/or suitable alloys may be used.

The stent is typically constructed so that material of the typically inner and typically more pliable net cannot inadvertently become inserted into the openings of the important branching vessels, if the device is inserted into the aortic arch, for example. The device may feature a plurality of layers, including at least an inner layer and an outer layer. The inner layer is typically constructed of a pliable net, with relatively small openings, so that blood can flow through the net freely, but not emboli. The size of the mesh is typically such that it permits passage of blood and micro-emboli, for example according to the organ system, which is to be protected.

The distal part of the net is typically narrowed, and more typically features two layers of the same material. The free edges may be reinforced with, for example, a weave of metallic thread, such as gold. The layers therefore typically form a basket-like structure with overlapping layers at one end, which are not sealed, but instead may optionally be opened upon retrograde motion through the distal end of the net structure. Therefore, emboli can be trapped in the net structure, as they typically float in the blood flow, but diagnostic and/or therapeutic catheters may optionally enter the aortic arch (or any other blood vessel in which the device of the present invention is installed) through the distal end of the net. In other words, in such an embodiment, the distal part of the net forms a trap for emboli, with a one-way valve, allowing passage of medical instruments.

A temporary component may be added to the device, for example for use during heart and aortic surgery, with extracorporeal circulation after the device has been inserted to the blood vessel. Such a temporary component is may be implemented as, for example, an inner mesh, which is optionally inserted into the device in order to trap micro-emboli during surgery. This mesh with the entrapped contents is then typically removed at the end of the surgical procedure.

The device according to one embodiment of the present invention may be insertable into a blood vessel in a wrapped or compressed form by, for example, using a catheter, according to, for example, the 'Seldinger Technique'. The deployment site may be optionally determined by any number of imaging methods, including but not limited to X-ray fluoroscopy, intravascular ultrasound, or echocardiography, MRI (magnetic resonance imaging), angioscopy, CT (computerized tomography) scan, and/or any other suitable imaging technology. Another optional mode of deployment is surgical, by direct insertion of the catheter carrying the device through a puncture of the targeted vessel in proximity to the deployment site.

The device of the present invention may optionally serve as a platform for carrying physiologic, hematological, biochemical and so forth micro-sensors. Enabling continued monitoring of one or more parameters, such as temperature, blood pressure, heart rhythm, blood flow ('cardiac output'), pH, electrolytes, blood sugar, blood LDL etc. These microprocessors typically transmit the data (for example) wirelessly to an outer monitoring device, as needed. The device can be loaded by coating or small aggregates, to serve as an internal "docking station" to release drugs, hormones, genes and so forth either automatically or by sensor-reactor programming, servomechanism or external control.

The device and method are particularly useful in preventing blockages of flow to the brain, but have other uses as well.

BRIEF DESCRIPTION OF THE DRAWINGS

The invention is herein described, by way of example only, with reference to the accompanying drawings, wherein.

DESCRIPTION OF THE EMBODIMENTS

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the present invention provide for a device for protecting body organs such as the brain and hence bodily tissues, against damage caused by particulate matter such as an embolus. The device is typically in a stent configuration, for insertion in a large artery such as the aorta (as shown below), structured as a filter and/or with filtering material. Other configurations are possible. The filtering structure is typically made of at least one layer of mesh, which is attached to the arterial wall. Other numbers of mesh layers may be used. Typically only part of the device is attached (for example at a reinforcing structure or a ring structure).

Devices according to embodiments of the present invention typically includes a plurality of layers. The outer layer is typically made of a typically dilatable and/or otherwise self-expanding tubular structure or stent. The stent is typically not required to dilate the artery and serves as an outer skeleton, stabilizer and protector of the inner structure. Other outer structures may be used. This tubular structure is typically anchored to the vascular wall after dilation to the size and shape of the vessel, or at least to the diameter of the blood vessel and possibly, to ensure good contact and stabilization. More typically, anchoring components, such as fine pins, are employed for anchoring the device to the tissues of the vascular wall, although such anchoring components need not be used. The material of which the device is constructed may optionally be metallic, but other suitable materials may be used.

Typically, the device includes a first cage-like structure for holding a net, in which the net is able to filter the particulate matter. The net (and possible other components) is constructed of a flexible, fine thread which is suitable for insertion into the body and/or for medical use. Other materials may be used, such as titanium, gold, and/or suitable alloys.

The outer stent is typically constructed such that material of the net cannot inadvertently become inserted into the openings of the important branching vessels, if the device is inserted into the aortic arch, for example. More typically, the net features a plurality of layers, including at least an inner layer and an outer layer. The inner layer is typically constructed of a pliable net, with relatively small openings, so that blood can flow through the net freely, but not certain particulate matter such as emboli. The size of the mesh is typically in a range which permits emboli that may pose a danger to organs in the body to be trapped, and is more typically selected according to the location of the device within the body.

The distal part of the net is optionally and typically narrowed, and more typically features two layers of the same material. The free edges are typically reinforced with a reinforcing structure, such as weaving gold thread or thread or material of, typically, any relatively heavier. More typically, such reinforcement causes that portion to be somewhat thicker and heavier, such that the ends of the net remain distal to the cage-like outer structure and also remain open at the distal part. The layers therefore typically form a basket-like structure with overlapping layers at one end, which are not sealed, but instead may optionally be opened upon retrograde motion through the distal end of the net structure. Therefore, emboli or other particulate can be trapped in the net structure, but diagnostic and/or therapeutic catheters may optionally enter the aortic arch (or any other blood vessel in which the device of the present invention is installed) through the distal end of the net. In other words the distal part of the net forms a trap for emboli or other particulate, with a one-way valve, allowing passage of medical instruments.

This distal structure may be suitable for passage of, for example, therapeutic endovascular catheters for removal of entrapped debris and clots by way of mechanical clot extraction, ultrasonic cavitation, LASER, local delivery of thrombolytic agents such as t-PA for example, and other suitable therapies. The distal structure can also optionally be used for insertion of cardiovascular angiographic catheters as well as therapeutic balloon catheters, drills, stents and so forth.

In one embodiment, a temporary component may be added to the device, for example for use during heart and aortic surgery, after the device has been inserted to the blood vessel. Such a temporary component is typically implemented as an inner mesh, which is optionally inserted into the device in order to trap, for example, micro emboli during surgery. This mesh with the entrapped contents is then typically re-wrapped, and removed at the end of the surgical procedure.

A device according to an embodiment of the present invention is typically insertable into a blood vessel in a folded or compressed form by using a catheter, according to the 'Seldinger Technique'. The deployment site is optionally determined by any number of visualization methods, including but not limited to X-ray fluoroscopy, ultrasound (or echocardiography), MRI (magnetic resonance imaging), direct angioscopy, near infrared angiology, intra-vascular ultrasound, CT (computerized tomography) scan, and/or any other suitable imaging technology. Another optional mode of deployment is surgical, by direct insertion of the catheter carrying the device through a puncture of the targeted vessel in proximity to the deployment site.

A device according to an embodiment of the present invention may optionally serve as a platform for carrying, for example, physiologic micro-sensors, such as temperature, blood pressure, heart rhythm, blood flow (e.g., 'cardiac output'), pH, electrolytes, blood sugar, blood LDL etc. These microprocessors typically transmit the data, typically wirelessly, to an outer monitoring device, as needed.

In one embodiment, due to the relatively large diameter of the device as a whole, a very large embolus is typically required to impede blood flow across the entire device. Smaller emboli, which would be caught in the filter of the device, might dissolve spontaneously or, for example, could be treated with drugs. Typically, minute micro-emboli are allowed to pass through the device, as they should not cause major damage to organs. The size of the mesh can be adjusted as suitable.

Embodiments of the present invention may have various medical applications, including but not limited to, prevention or treatment of blockage of any blood vessel or any other bodily passage, such as the carotid artery, aorta, veins and so forth; prevention or treatment of blockage of any blood vessel or any other bodily passage which is secondary to medical treatment, such as catheterization; and use of the device to overcome medical conditions which may cause or exacerbate the formation of blood clots in the patient. Embodiments may also optionally used as an adjunct during surgery, for example with the addition of a temporary filter in the device with mesh having relatively small holes; this temporary filter maybe removed after surgery.

Figure 1:
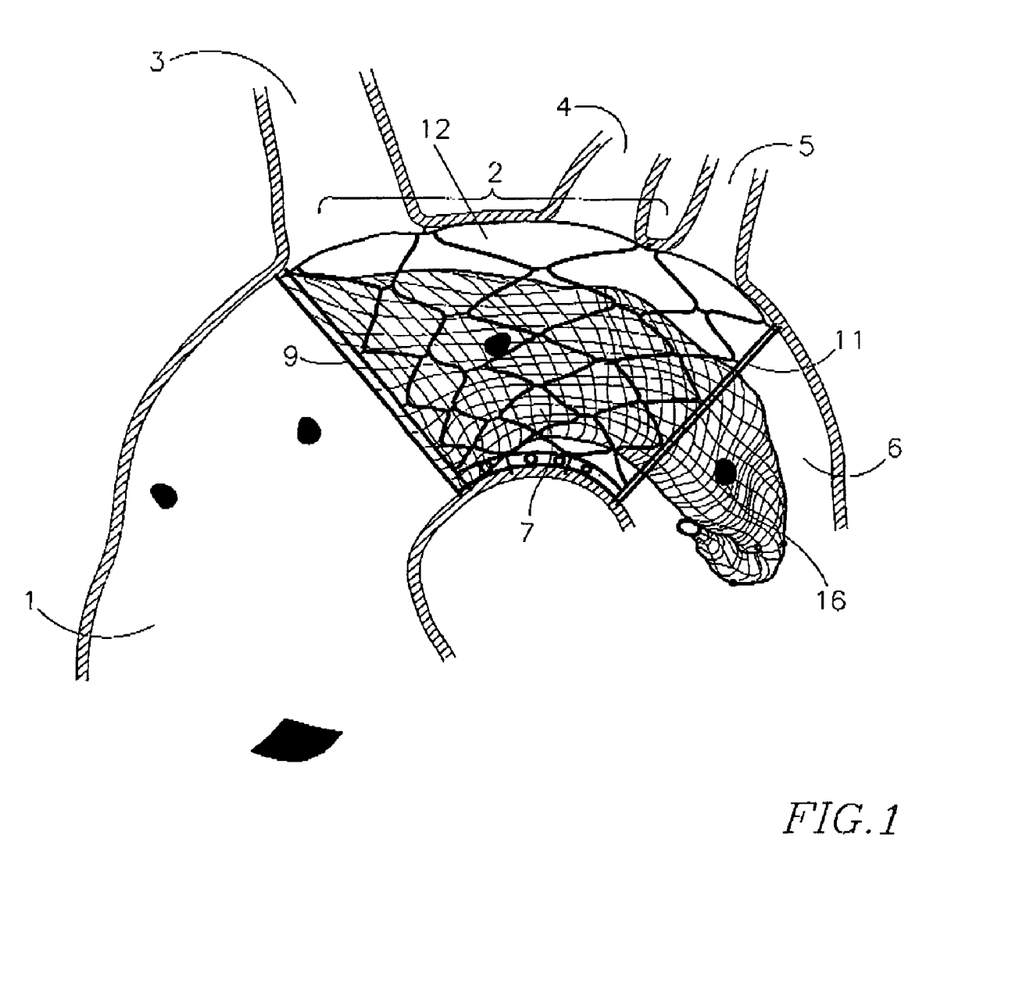
FIG. 1 is a schematic diagram of a device according to an embodiment of the present invention, shown inserted into the ascending aorta.

FIG. 1 is a schematic diagram of a device according to an embodiment of the present invention, shown inserted into the ascending aorta. As shown, a device 7 is inserted into ascending aorta 1 for the purposes of illustration only and without any intention of being limiting. Other methods of insertion and positions of insertion and use may be used. Device 7 also may be suitable for, for example, insertion into a number of major blood vessels in the body. As shown in FIG. 1, when inserted into ascending aorta 1, device 7 is typically placed beneath, and physically adjacent to, brachiocephalic artery 3, left carotid artery 4 and left subclavian artery 5. Device 7 may optionally attenuate movement of ascending aorta 1 slightly with each blood pulse, but without significantly impeding the action of aorta 1.

In one embodiment, device 7, or at least a portion thereof, also extends into the descending thoracic aorta 6. This placement provides high protection for different organs in the body. Briefly, this placement prevents particulate matter (of at least a size to be trapped by device 7) from entering the brain. In addition, by preventing entry of particulate matter to the brain, transmission of such particulate matter to more distal organs, such as the kidneys and liver for example, is also prevented. Also, this location enables trapped material to be more easily and more safely removed.

In the embodiment shown, device 7 typically features an outer or external structure 2, which is more typically in the structure, construction, configuration or shape of a stent. Such a shape is typically tubular or cylindrical, and fits closely to the surface of the blood vessel into which device 7 has been inserted, which is ascending aorta 1 in this example. External structure 2 is typically capable of insertion into a blood vessel. Outer or external structure 2 is typically a cage-like structure, featuring typically a stent which acts as both an external support skeleton and also as secondary physical protection. Furthermore the stent may prevent the net from entering a branch and potentially occluding the blood flow. The stent typically features relatively large apertures, as shown with regard to FIG. 2. Typically, the stent or outer structure includes holes or openings of a first size, and the inner mesh or filter or structure includes holes or openings of a second size, the first size being typically larger than the second size. Typically the size of the apertures of the net may be smaller in the part facing the arterial branch to be protected. The size of the holes in the net are typically small enough to filter almost all emboli causing significant disease, but allowing free flow of blood. The pressure gradient across the device in the blood stream typically causes only minor pressure-drop (less than 10%); other pressure drops are possible. Other configurations and shapes, and other mesh sizes, may be used. For example, the external structure may be wire frame, such as the one depicted in FIG. 4 below. Such a structure may include a number of bends.

In one embodiment, outer or external structure 2 includes 'void' areas or spaces facing certain vessel openings, such as on the 'top' side facing the aortic arch vessels, namely the right innominate artery (also called thee brachiocephalic artery(, the left carotid artery, and the left subclavian artery). Other positions for such voids may be used, and voids need not be used.

In one embodiment, outer or external structure 2 is a 'bent' tubular stent with, typically, a few parallel bars which are interposed by, typically, a few lateral thin wires to maintain physical form and strength. In one embodiment, the total length of outer or external structure 2 complies with the distance in the body, and its width when dilated is 20–30 mm, according to the individual aortic width. Other dimensions may be used.

In one embodiment, the geometry of the external structure 2 enables easy folding. The external structure 2 typically includes an outer diameter of less than 9 French or 3 mm, but other dimensions may be used.

Device 7 also typically includes an internal structure such as a filter or net 16 for trapping particulate such as emboli, which is typically located within, and anchored to, external structure 2. Other trapping or filtering structures may be used. Internal filter or net 16 typically features a relatively fine net which functions as a filter, and more typically extends beyond external structure 2. Such extension need not be used. Internal filter or net 16 is typically flexible.

Typically, the internal structure is kept a certain lateral distance from the walls of the surrounding artery. This may help in preventing flow into branch vessels from being impeded.

When used in the position shown, such an extension of the material of internal net 16 may prevent any trapped particulate matter from blocking blood flow to those previously described major blood vessels, as well as supporting the continued flow of blood through the entirety of device 7. Internal net 16 also most typically features a tapered shape, particularly for the portion which extends beyond external structure 2, again for the purpose of preventing particulate matter from blocking the flow of blood through device 7 and/or the blood vessel itself. In alternate embodiments, other internal structures may be used, such as other filters or nets. The internal structure may have a different shape or configuration.

In one embodiment, an electric charge may be placed on the device, so that, for example, blood components such as proteins do not collect on or adhere to the external structure 2. For example, an electric charge can be achieved by the addition of metals and/or polymers that are naturally charged, or, alternately, by incorporating piezo-electric materials or piezo-electric cells which may generate charges (for example, up to 100–200 milivolts). Such piezo-electric materials or piezo-electric cells may generate electricity or electric charges by even minor physical changes in position, caused by, for example, the changes in blood pressure during the cardiac cycle (systolic/diastolic pressure).

Figure 2A:
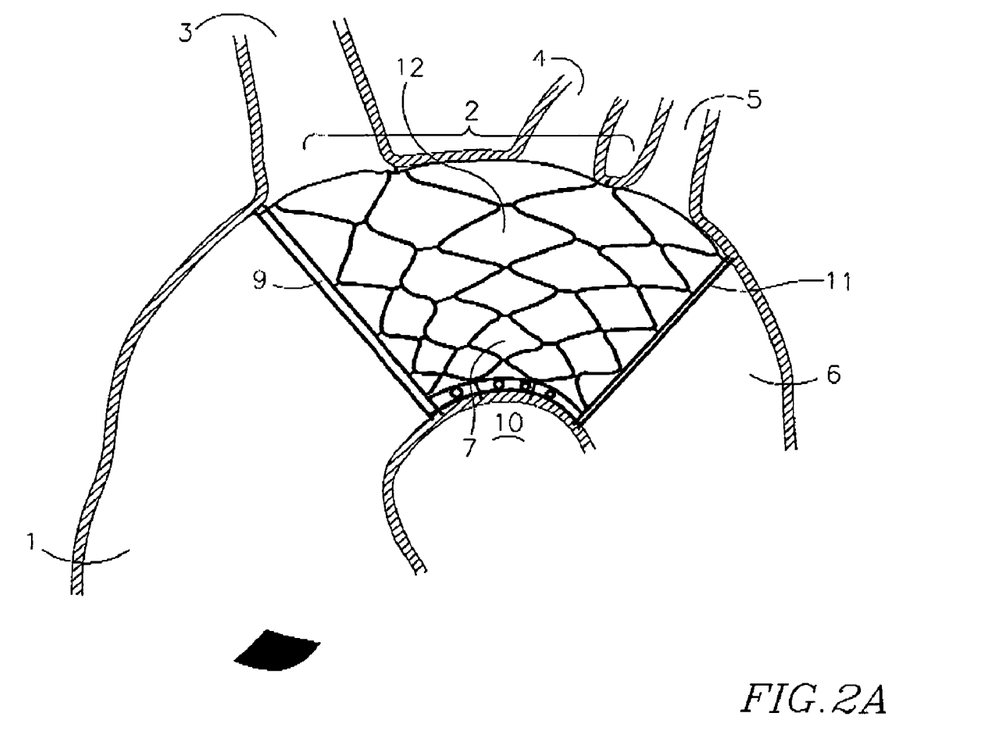
FIG. 2a shows the outer mesh layer of the device of FIG. 1 according to an embodiment of the present invention.

FIG. 2 shows one embodiment of the outer mesh layer of the device of FIG. 1, showing the components separately from the remainder of the device. External structure 2 typically features a mesh 12 having relatively large apertures or holes, for trapping relatively large emboli and/or other particulate matter. Other sizes and shapes may be used.

External structure 2 is optionally and typically anchored to the wall of the aorta 1. Such anchoring structure may include, for example, at least one pin 13. Other mounting methods and devices may be used.

Figure 2B:
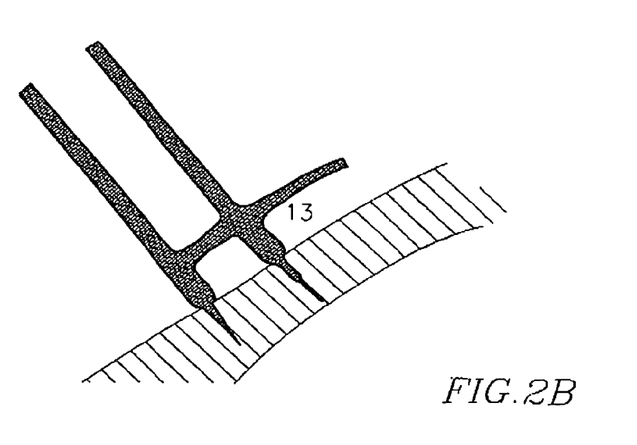
FIG. 2b depicts details of the device of FIG. 1 according to an embodiment of the present invention.

Typically, external structure 2 includes at least one, and more typically a plurality of, support interconnection components, shown as a proximal support interconnection component 9 and a distal support interconnection component 11. Interconnection components 9 and 11 may be, for example, rings, or sutures but may be other types of structures. Other types and numbers of support interconnection components may be used. A plurality of pins 13 (shown in detail FIG. 2A) are more typically used to anchor external structure 2 to the wall of ascending aorta 1. Pin(s) 13 typically attach each of proximal support interconnection component 9 and distal support interconnection component 11 to the wall of ascending aorta 1.

Figure 3A:
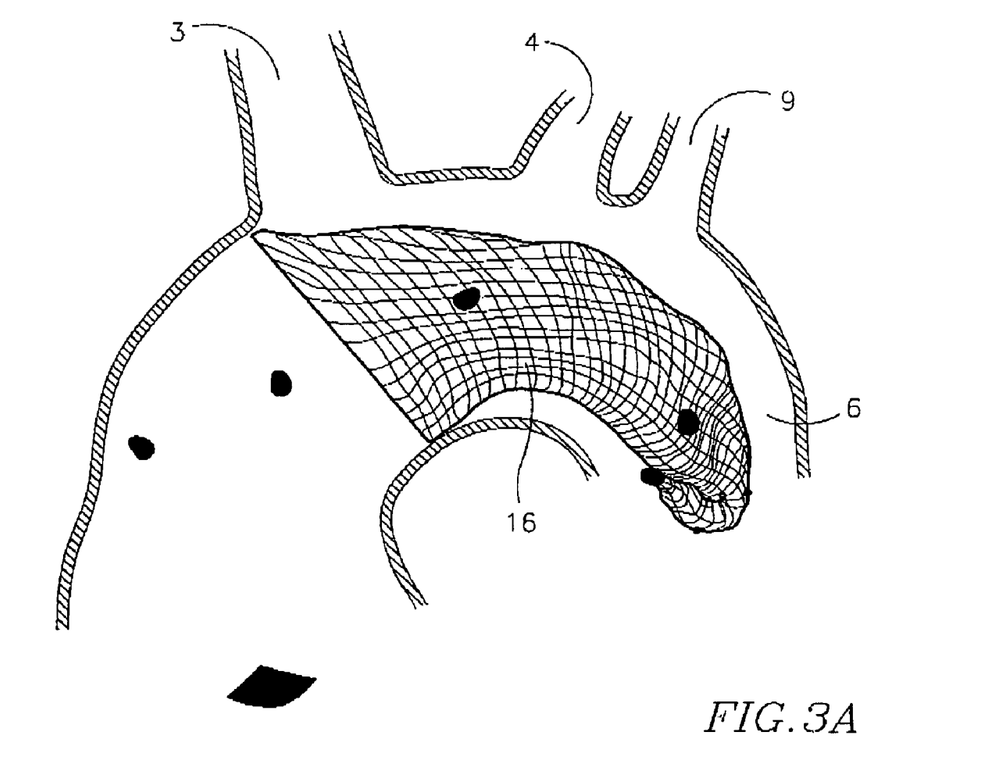
FIG. 3a shows the inner mesh layer of the device of FIG. 1 according to an embodiment of the present invention.

External structure 2 also typically features one or a plurality of connections between the outer stent and the inner net for connecting mesh 12 to the internal net (FIG. 3), to prevent the latter from being dislodged from the blood vessel, and/or from being moved within the blood vessel. Such movement might inadvertently block blood flow to one of the other arteries shown in FIG. 1, for example. Other suitable connection methods may be used.

In one embodiment, external structure 2 features a plurality of devices such as micro sensors 14 and 15 for sensing physiological functions or parameters, such as, for example, blood pressure, ECG, heart rate, pH values, temperature, velocity, oxygen saturation and content, as well as for any biochemical, endocrine, or hematological status including, for example, clotting mechanism and factors, or any drug concentration (see also FIG. 2A). Micro-sensors 14 and 15 may be, for example, attached to a support platform 10. Support platform 10 may be thicker and stiffer, to conform to the natural shape of the aortic arch. Other methods of attaching additional devices may be used, having other configurations. Micro sensors could be coupled, for example, with adjusted release mechanisms for, for example, glucose, insulin, or other substances.

Figure 3B:
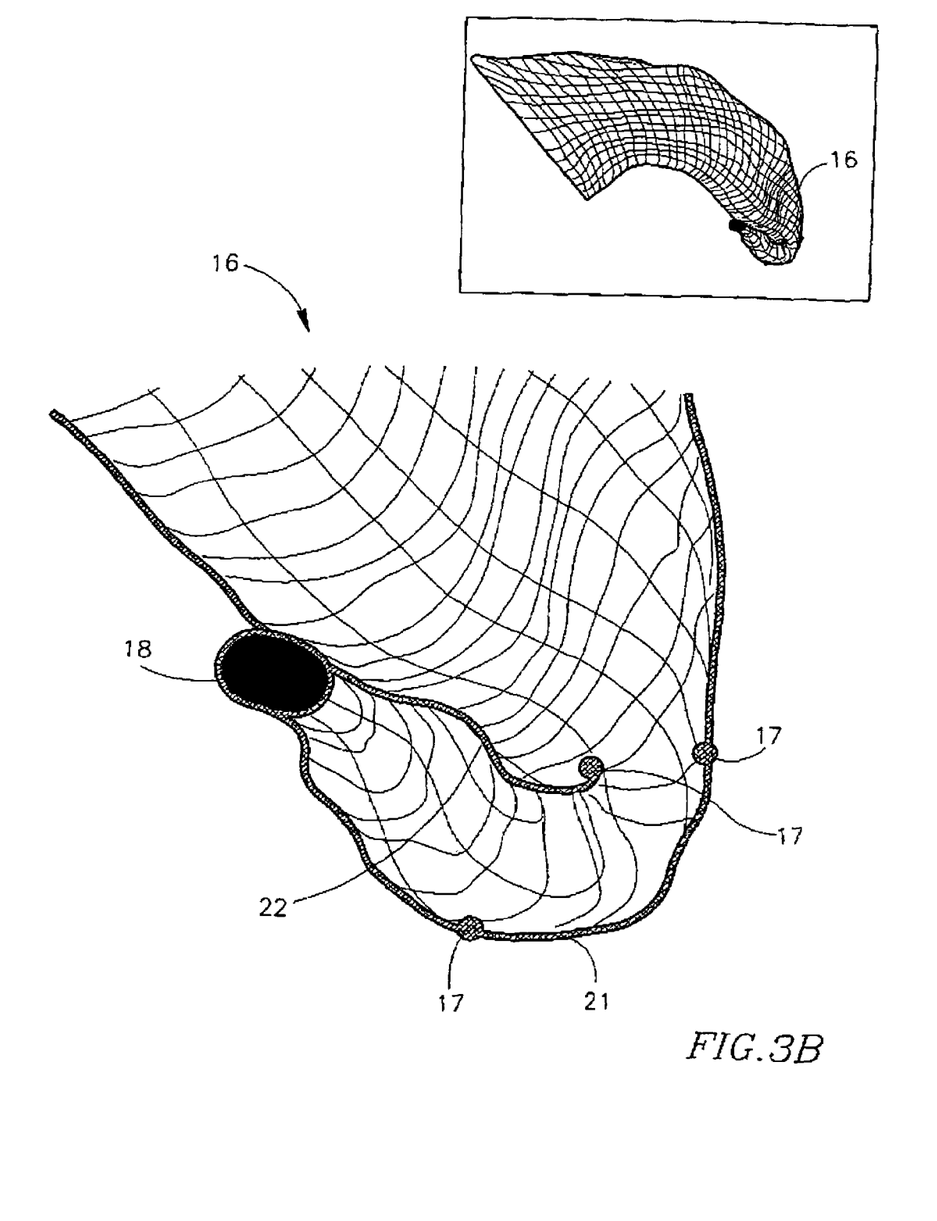
FIG. 3b details of the device of FIG. 1 according to an embodiment of the present invention.

FIG. 3 shows one embodiment of the inner mesh layer of the device of FIG. 1, featuring the internal filter or net 16. Optionally and more typically, the distal end of internal net 16 is constructed as a one-way valve 18, made of, for example, two layers, flaps or leaflets 21 and 22 of the net material. The overlap enables retrograde insertion of catheters. The two layers or leaflets 21 and 22 of the net or filter material typically feature weights 17, for prevention of movement of the distal end of internal net 16 backward (see also detail FIG. 3A). One leaf 21 or layer may be extend further than the other, curving around the tip of the net 16. Other configurations for the inner mesh layer may be used. For example, such one-way valve need not be used, and weights 17 need not be used. Furthermore, if a valve is included, the valve may include other configurations.

In one embodiment, internal net 16 is made of two or more leaves or flat portions, typically connected along the sides, tapered towards their outlet ends, with one slightly longer than the other, and not connected at the distal end. One leaflet 21 may be longer than the other, curving around the tip. The two leaflets 21 and 22 may be interconnected at multiple sites (points), but spaced at the distal end, to form, for example, a valve—allowing easy passage from the distal end but not from the lumen. An 'active valve' may thus be formed. Particles can not pass distally but a catheter can be passed from the distal end proximally. Other shapes for the leaflets 21 and 22 may be used, and a leaf structure need not be used.

This distal structure may be suitable for passage of, for example, therapeutic endovascular catheters for, for example, removal of entrapped debris and clots by way of mechanical clot extraction, ultra-sonic cavitation, LASER, local delivery of thrombolytic agents such as t-PA for example, and other suitable therapies. The distal structure can also optionally be used for insertion of cardiovascular angiographic catheters as well as therapeutic balloon catheters for Valvuloplasty, drills, stents Electrophysiology catheters, clot removal device and so forth.

Figure 4:
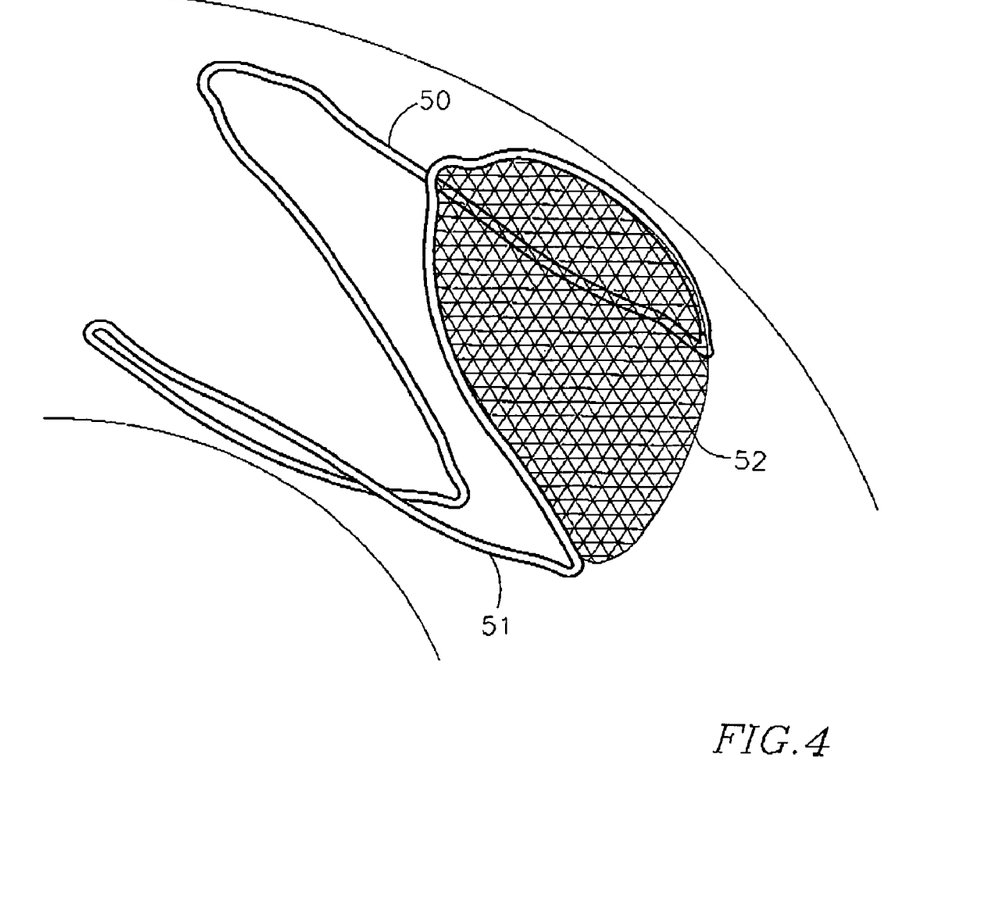
FIG. 4 depicts an embodiment where an inner filter or net provides focal coverage for an area to be protected.

In a further embodiment, an inner filter or structure may be shaped and sized to protect only a portion of the area within the outer structure. Such a "focal" filter may enable free passage through a portion of the outer structure of devices such as catheters, for example to aid in procedures of angioplasty, percutanous valvuloplasty, or other procedures. FIG. 4 depicts an embodiment where an inner filter or net provides focal-coverage for an area to be protected. Referring to FIG. 4, outer structure 50 includes an inner net or filter 52, which covers only a portion of the area of the outer structure. For example, inner filter 52 may protect or filter blood flow to the brain when properly inserted. Outer structure 50 is a wire frame as opposed to a stent like structure, but may also be a stent like structure.

Typically, inner filter 52 faces one branch for which protection is desired, such as (given one possible configuration and placement) one of the right innominate artery, the left carotid artery, and/or the left subclavian artery. More than one such filter may be included, covering more than one branch, or one filter may cover more than one branch. Such an embodiment may, for example, protect the brain (vessels leading to the brain) but not other branches or areas, such as the distal branches (e.g., the renal arteries, femoral arteries, etc). In alternate embodiments, configurations may differ, and if placement differs, different areas may be protected. Outer structure 50 may alternately include a filter as described in FIGS. 1–3.

The wire 51 forming outer structure 50 typically contacts the surrounding blood vessel at every or almost every point along the wire 51, but need not. In the embodiment shown, the outer structure 50 is a "tripod" structure with three main sections or lobes, but may have four or other numbers of sections. Such an outer structure 50 may be particularly suited for easy folding and positioning, by, for example, being wrapped or folded to a relatively small size of, for example, 9–10F, such that it is passable through the femoral artery. Other insertion methods may be used.

In one embodiment, a device according to an embodiment of the present invention can be inserted as, for example, protection from brain emboli prior to an invasive intracardiac procedure, such as balloon aortic valvuloplasty, balloon mitral valvuloplsty, electrophysiological studies, with or without ablation of ectopic rhythmic sites, insertion of automatic defibrilators, percutaneous valve repair or replacement, or other procedures. Embodiments of the device can be used, for example, in patients with severe aortic atheroma for brain protection during routine heart catheterization, or for endovascular "cleaning" of atheromatous or thrombotic material. Such an embodiment could be used in patients with high risk or propensity to form intracardiac clots, for example patients with hematological disease, arrhythmia of the heart, artificial heart patients, assist-device patients, mechanical valve replacement patients, patients following intracardiac repair of a pathology, or patients with congenital heart disease such as patent foramen ovale, and so forth.

Figure 5:
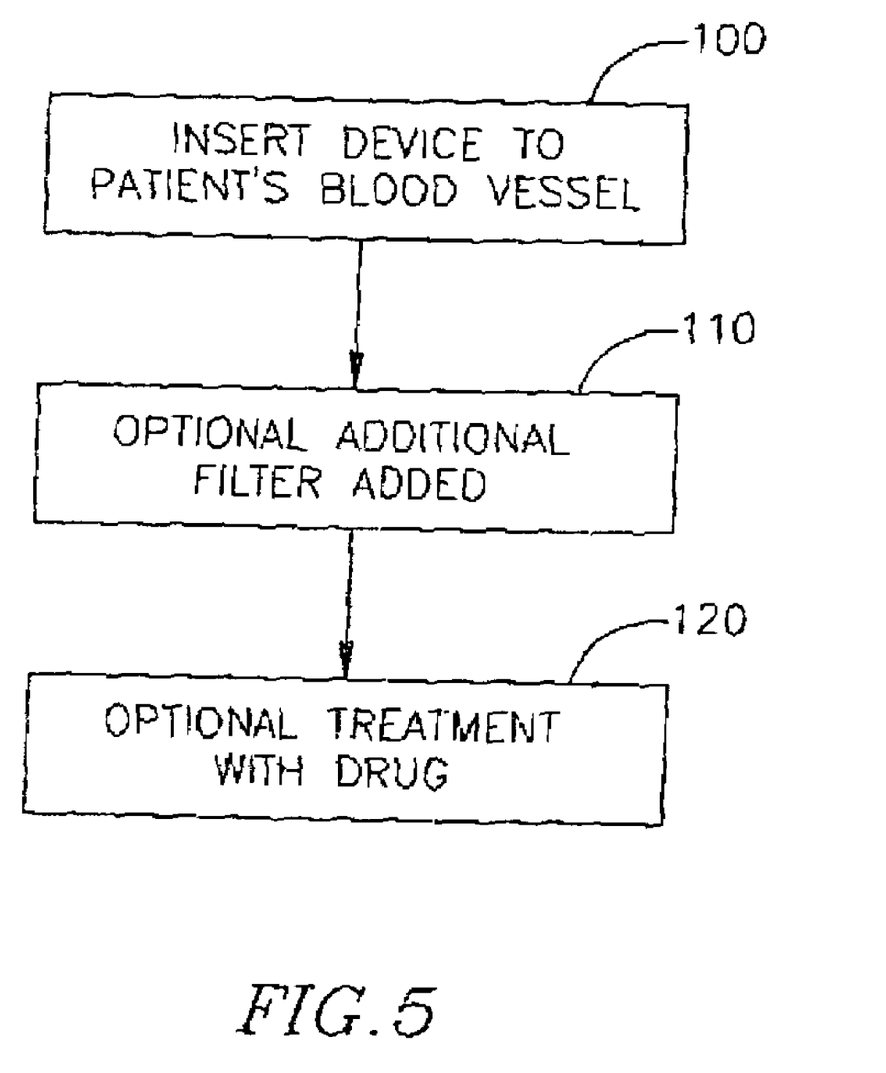
FIG. 5 is a flowchart depicting a series of steps according to one embodiment of the present invention.

FIG. 5 is a flowchart depicting a series of steps according to one embodiment of the present invention. Referring to FIG. 5, in step 100, a device, such as an embodiment of the device described above, is inserted into a patient's blood vessel. In one embodiment, the insertion may be performed during an insertion procedure, and the device may remain in the blood vessel after the insertion procedure is complete.

In one embodiment, the device is inserted in a "wrapped" form. The outer diameter of the wrapped device enables introduction via a peripheral artery, such as the common femoral artery, using the OTW technique or Seldinger technique. An alternate mode of insertion may be, for example, surgical. The surgeon can insert the device OTW through a direct needle puncture of the artery. Other insertion methods may be used.

In step 110, optionally, an additional filter may be inserted into or otherwise connected to the device, for example during the duration of a surgical procedure. The additional filter is typically removed after the surgical procedure is complete.

In step 120, optionally, the patient may be treated with a drug, for example, a drug for endocarditis or blood clots.

Other steps or series of steps may be performed. For example, the method may additionally include dilating a valve of the patient with a catheter. In addition, the inner filter may be removed or replaced without removing the outer structure.

A device according to an embodiment of the present invention can be used, for example, temporarily for acute conditions. For example, the device can be inserted for the duration, or the known duration, of the condition. For example, the device may be inserted temporarily to protect against cardio embolic stroke or embolic stroke. Currently, patients with acute myocardial infarction (AMI) show an incidence of 35% of clots in the heart (Left Ventricle), and 2% will have major stroke or death from this cardio embolic stroke or embolic stroke.

In alternate embodiments, the device can be coated by a structure or substance for better tissue adaption and biocompatibility. The device can include pharmacologic or genetic agents, thus serving as a platform for controlled release of any substance, where it is needed.

Other conditions may warrant insertion. In other embodiments, the device may be inserted for a long-term period, or permanently. In further embodiments, the device may be inserted for the duration of a procedure or treatment.

In further embodiments, portions of the device, such as the inner filter, may be wholly or partially biodegradeable.

It will be appreciated by persons skilled in the art that the present invention is not limited to what has been particularly shown and described hereinabove . Rather the scope of the present invention is defined only by the claims which follow:

What is claimed is:

1. A device for filtering particulate matter in a bodily passage, the device comprising:
    an outer structure capable of insertion into the bodily passage;
    an inner filter connected to said outer structure, a distal end of said filter having a one way valve to allow passage through said inner filter of a medical instrument said valve comprising a plurality of leaflets, a first of said plurality of leaflets extending over a second of said plurality of leaflets, said first of said plurality of leaflets curving over said distal end of said inner filter; and a weight attached to a leaflet of said plurality of leaflets to prevent backward movement of said distal end of said filter.

2. The device of claim 1, wherein said inner filter includes at least a portion extending beyond said outer structure.

3. The device of claim 1, wherein said inner filter includes at least a partially flexible portion.

4. The device of claim 1, wherein said inner filter is flexible.

5. The device of claim 1, wherein said outer structure includes a mesh.

6. The device of claim 1, wherein said outer structure includes a stent.

7. The device of claim 1, wherein said outer structure includes holes of a first size and said inner filter includes holes of a second size, said first size being larger than said second size.

8. The device of claim 1, wherein the outer structure is capable of insertion into a blood vessel.

9. The device of claim 1, comprising an anchoring structure.

10. The device of claim 1, comprising an anchoring pin capable of anchoring the device to a blood vessel.

11. The device of claim 1 wherein the inner filter extends over only a portion of the outer structure.

12. The device of claim 1 wherein the outer structure is a wire frame.

13. The device of claim 1 wherein the inner filter is comprised of a plurality of flat portions.

14. A device for filtering in a bodily passage, the device comprising:
    an outer structure capable of insertion into the bodily passage;
    an inner filter disposed within said outer structure and extending beyond said outer structure, a distal end of said filter having a one way valve to allow passage through said inner filter of a medical instrument, said one way valve comprising a plurality of leaflets, a first of said plurality of leaflets curving over said distal end of said inner filter; and
    a weight attached to a leaflet of said plurality of leaflets to prevent backward movement of said distal end of said filter.

15. A device for filtering in a bodily passage, the device comprising:
    an outer structure capable of insertion into the bodily passage; and
    an inner filter disposed within said outer structure and including at least two overlapping leaflets, a distal end of said filter having a one way valve to allow passage through said inner filter of a medical instrument, said one way valve comprising a plurality of leaflets, a first of said plurality of leaflets curving over said distal end of said inner filter; and
    a weight attached to a leaflet of said plurality of leaflets to prevent backward movement of said distal end of said filter.

16. A device for filtering in a bodily passage, the device comprising:
    an inner filter means for filtering particulate, a distal end of said filter having a one way valve to allow passage through said inner filter of a medical instrument;
    an outer stent means for holding said inner filter means, said one way valve comprising a plurality of leaflets, a first of said plurality of leaflets curving over said distal end of said inner filter; and
    a weight attached to a leaflet of said plurality of leaflets to prevent backward movement of said distal end of said filter.

17. A device for filtering particulate matter in a bodily passage, the device comprising:
    an outer structure for insertion into the bodily passage, said outer structure conforming to a shape of the bodily passage;
        an inner filter for being anchored to said outer structure and for filtering the particulate matter, said inner filter having a portion extending beyond said outer structure, said extended portion being at least partially flexible, a distal end of said filter having a one way valve to allow passage through said inner filter of a medical instrument, said one way valve comprising a plurality of leaflets, a first of said plurality of leaflets curving over said distal end of said inner filter; and
    a weight attached to a leaflet of said plurality of leaflets to prevent backward movement of said distal end of said filter.

18. The device of claim 17, wherein said extended portion comprises two overlapping leaflets.

19. The device of claim 17, wherein said outer structure has holes of a first size and said inner filter includes holes of a second size, said first size being larger than said second size.

* * * * *